United States Patent [19]
Broudy et al.

[11] Patent Number: 5,906,938
[45] Date of Patent: May 25, 1999

[54] METHOD OF RECONSTITUTING HEMATOPOIETIC CELLS USING MONOCLONAL ANTIBODIES TO THE STEM CELL FACTOR RECEPTOR

[75] Inventors: Virginia C. Broudy; Nancy Lin, both of Seattle, Wash.

[73] Assignee: Board of Regents of the University of Washington, Seattle, Wash.

[21] Appl. No.: 08/449,139

[22] Filed: May 24, 1995

Related U.S. Application Data

[63] Continuation of application No. 08/011,078, Jan. 29, 1993, Pat. No. 5,489,516, which is a continuation of application No. 07/681,245, Apr. 5, 1991, abandoned.

[51] Int. Cl.$^6$ .................................................. C12N 15/85
[52] U.S. Cl. ..................... 435/372; 435/325; 435/375; 530/413
[58] Field of Search .................................. 435/325, 372, 435/375; 530/413

[56] References Cited

U.S. PATENT DOCUMENTS

| | | | |
|---|---|---|---|
| 4,965,204 | 10/1990 | Civin et al. | |
| 5,061,620 | 10/1991 | Tsukamoto et al. | 435/7.21 |
| 5,081,030 | 1/1992 | Civin et al. | 435/240.2 |
| 5,489,516 | 2/1996 | Broudy et al. | 435/7.23 |

FOREIGN PATENT DOCUMENTS

| | | |
|---|---|---|
| 395355 | 10/1990 | European Pat. Off. . |
| WO 86/01533 | 3/1986 | WIPO . |

OTHER PUBLICATIONS

Andrews et al., J. Exp. Med. 169:1721–1731 (1989).
Andrews et al., J. Exp. Med. 172:355, (1990).
Ashman et al., Leukemia Res. 12:923–928 (1988).
Banchereau et al., Science 251:70–72 (1991).
Beidler et al., J. Immunol. 141:4053–4060 (1988).
Bensinger et al., J. Clin. Apheresis 5:74–76 (1990).
Berenson et al., Blood 76:509–515 (1986).
Blättler et al., Cancer Cells 1:50–55 (1989).
Bodine et al., Proc. Natl. Acad. Sci. USA 86:8897–8901 (1989).
Boyer and Roulland–Dussoix, J. Mol. Biol. 41:459 (1969).
Broudy et al., Blood 75:1622–1626 (1990).
Broudy et al., Proc. Natl. Acad. Sci. USA 85:6513–6517 (1988).
Butterfield et al., Leukemia Research 12:345 (1988).
Calame, Annual Rev. Immunol. 3:159–196 (1985).
Calvo et al., Biochem. J. 212:259–264 (1983).
Cambareri et al., Leukemia Res. 12:929–939 (1988).
Cawley et al., Cell 22:563–570 (1980).
Chang and Cohen, J. Bacteriol. 143:1141–1156 (1978).
Dick, Annals of the N.Y. Academy of Sciences 507:242–251 (1987).
Dillman et al., Cancer Research 48:6097–6101 (1988).
Ey et al., Immunochemistry 15:429 (1978).
Flanagan and Leder, Cell 63:185–194 (1990).

Frankel, Immunotoxins, Edited by, Kluwer Academic Publishers, Boston (1988).
Fritzberg et al. Proc. Natl. Acad. Sciences U.S.A. 85:4025 (1988).
Gadd and Ashman, Leukemia Res. 11:1329–1336 (1985).
Garvey et al., Methods in Immunology, Chapter 31, W.A. Benjamin, Reading, Massachusetts (1977).
Goff et al., Bioconjugate Chemistry 1:381–386 (1990).
Hamann et al., Abstracts of 197th American Chemical Society National Meeting, Dallas, Texas, U.S.A., Apr. 9–14, 1989, Abstract No. 71A.
Hill et al., Bone Marrow Transplant. 4:69–74 (1989).
Hnatowich et al., J. Nuclear Medicine 26:503–509 (1985).
Ho et al., J. Immunol. 135:3831 (1985).
Humm. J.L., J. Nuclear Medicine 27, 1490–1497 (1986).
Hunter and Greenwood Nature 194:495–496 (1962).
Kohler and Milstein, Nature 256:495–497 (1975).
Lerner et al., Blood 76 (Suppl):295a, (1990).
McMichael, Monoclonal Antibodies in Clinical Medicine 79–107, Academic Press Inc. (1982).
Moi et al., Cancer Research (Suppl.) 50:7895–7935 (1990).
Moolten, J. Natl. Con. Inst. 55:473–477 (1975).
Morrison and Oi, Annual Rev. Immunol. 2:239–256 (1984).
Morrison et al., Ann. N.Y. Acad. Sci. 507:187–198 (1988).
Morrison, Science 229: 1202–1207 (1985).
Mulligan and Berg, Proc. Natl. Acad. Sci. USA 78:2072–2076 (1981).
Mulligan and Berg, Science 209:1422–1427 (1980).
Munson and Rodbard, Analyt. Biochem. 107:220–239 (1980).
Nicola and Metcalf, J. Cell Physiol. 124:313–321 (1985).
Nowinski et al., Virology 93:111–126 (1979).
Oi and Morrison, BioTechniques 4:214–221 (1986).
Papayannopoulou et al., Blood 72:1029–1038 (1988).
Park et al., Blood 74:56–65 (1989).
Perrine et al., Biochem. Biophys. Res. Comm. 164:857–862 (1989).
Press et al., J. Clin. Oncol. 7:1027–1038 (1989).
Qiu et al., EMBO J. 7:1003–1011 (1988).
Reichman et al., Nature 332:323–327 (1988).
Rhodes et al., J. Nuclear Medicine 21, 54 (1980).
Sahagan et al., J. Immunol. 137:106601074 (1986).
Santoli et al., J. Immunology 139:3348, (1987).
Scheinberg et al., Oncology 1, 31–37 (1987).
Schwartz J., Nuclear Medicine 28, 721 (1987).
Sevier, Clinical Chemistry 27: 1797 1806 (1981).

(List continued on next page.)

*Primary Examiner*—Sheela Huff
*Assistant Examiner*—Julie E Reeves
*Attorney, Agent, or Firm*—Robert B. Winter; Steve M. Odre; Ron K. Levy

[57] ABSTRACT

The present invention relates to monoclonal antibodies specific for a cell receptor specific for human stem cell factor (hSCF) as well as pharmaceutical compositions containing such monoclonal antibodies and uses of such monoclonal antibodies for the isolation and reconstitution of hematopoietic cells expressing the stem cell factor receptor.

18 Claims, 7 Drawing Sheets

OTHER PUBLICATIONS

Sugiura et al., Proc. Natl. Acad. Sci. U.S.A. 86:7672–7676 (1989).
Thorpe et al., J. Natl. Cancer Inst., 79:1011 (1987).
Uhr et al., Prog. Clin. Biol. Res. 288:403–412 (1989).
Vitetta, Sience 238: 1098–1104 (1987).
Weir, Handbook of Experimental Immol. 2: 55.1–55.18 (1986).
Yarden et al., EMBO J. 6:3341–3351 (1987.
Zsebo et al., Cell 63:213–224 (1990).
W. E. Paul, Ed., Fundamental Immunology, p. 242, Raven Press NY Chapter 8, 1993.
Tanaka et al Microbiol Immunolog vol. 29 (10) 959–972, 1985.
Gueson et al Immunochemistry vol. 14 443–447, 1977.
Majumder et al Molecular and Cellular Biology vol. 8 No. 11 4896–4903, 1988.
Lerner et al Blood 76 Supplement 295a, 1990.
Borudy et al Blood vol. 88 No. 1 75–81, Jul. 1996.
Zsebo et al Cell vol. 63 213–224, 1990.
Sevier et al Clin Chem col. 27 No. 11 1797–1806, 1981.
Gadd et al Leukemia Research vol. 9 No. 11 1329–1336, 1985.
Ashman et al., Leukemia Res. 12:923–928 (1988).
Cambaseri et al., Leukemia Res. 12: 929–939 (1988).
Gadd and Ashman, Leukemia Res. 9: 1329–1336 (1985).
Majumder et al., Mol Cellular Biology 8:4896–4903 (1988).
Yarden et al., EMBO J. 6:3341–3351 (1987).
Lerner et al., Blood 76 (Suppl.):295a (1990).

METHOD OF RECONSTITUTING HEMATOPOIETIC CELLS USING MONOCLONAL ANTIBODIES TO THE STEM CELL FACTOR RECEPTOR

This is a continuation of U.S. Ser. No. 08/011,078 filed Jan. 29, 1993, U.S. Pat. No. 5,489,516, which is a continuation of U.S. Ser. No. 07/681,245, filed Apr. 5,1991, now abandoned.

BACKGROUND OF THE INVENTION

The present invention relates to monoclonal antibodies specific for a cell receptor that binds human stem cell factor (hSCF), as well as pharmaceutical compositions containing such monoclonal antibodies and uses of such monoclonal antibodies.

Stem Cell Factor (SCF) is a growth factor that stimulates the proliferation of pluripotent hematopoietic progenitor cells. It has been produced recombinantly in *E. coli* and various mammalian cells [Zsebo et al., *Cell* 63:195–212 (1990); and PCT Application No. US90/05548, filed Sep. 28, 1990].

The proto-oncogene c-kit has recently been identified as the receptor for SCF [Zsebo et al., *Cell* 63:213–224 (1990)]. Prior to identification of c-kit as the ligand for SCF, the c-kit receptor was known to exist [Yarden et al., *EMBO J.* 6:3341–3351 (1987); Qiu et al., *EMBO J.* 7:1003–1011 (1988); Flanagan and Leder, *Cell* 63:185–194 (1990)].

Polyclonal antibodies directed against the murine c-kit have been reported [*Cellular Biology* 8:4896–4903 (1988)], but it is not known whether these antibodies will cross react with the human c-kit, whether they will block binding of SCF to its receptor, or whether they will affect cell growth. A polyclonal antibody raised against a human c-kit carboxy terminal peptide has also been reported [*EMBO J.* 6:3341–3351 (1987)], but these antibodies would not block SCF binding to the receptor. A monoclonal antibody that recognizes human SCF receptors has been reported [Lerner et al., *Blood* 76 (Suppl):295a, (1990); Ashman et al., *Leukemia Res.* 12:923–928 (1988); Cambaseri et al., *Leukemia Res.* 12:929–939 (1988); Gadd and Ashman, *Leukemia Res.* 11:1329–1336 (1985)].

Thus, until the existence of the present invention, the prior art has not been able to obtain a monoclonal antibody to the c-kit receptor with any expectation that such a monoclonal antibody would possess the ability to block the binding of the c-kit ligand, SCF.

This research is partially funded by the United Sates Government through National Institute of Health Grant P01-DK-31232 and the American Cancer Society Grant JFRA217.

SUMMARY OF THE INVENTION

The present invention relates to a monoclonal antibody comprising a monoclonal antibody having an ability to bind to an SCF receptor. Preferably, the binding of the monoclonal antibody to the SCF receptor will also inhibit binding of an SCF molecule to said SCF receptor. Preferably, the SCF and the SCF receptor will be of human origin.

In another aspect of the present invention, the SCF receptor monoclonal antibodies are used in a method of purifying hematopoietic cells comprising the steps of:
(a) exposing a mixture of cells to such monoclonal antibodies;
(b) separating cells that bind to said monoclonal antibodies from cells that do not bind to said monoclonal antibodies.

In another aspect of the present invention, the hematopoietic cells purified with the SCF receptor monoclonal antibodies are used in a method of reconstituting hematopoietic cells comprising bone marrow transplantation.

In another aspect of the present invention, the hematopoietic cells purified with the SCF receptor monoclonal antibodies are used in a method of gene therapy comprising retrovirally-mediated gene transfer into the purified cells.

Another aspect of the present invention relates to a method of separating normal cells from neoplastic cells comprising the steps of:
(a) exposing a mixture of cells comprising normal cells and neoplastic cells to a monoclonal antibody according to the present invention;
(b) separating normal cells from neoplastic leukemia cells based upon a differential in numbers of SCF receptors on normal cells and neoplastic leukemia cells.

Another aspect of the present invention relates to use of the SCF receptor monoclonal antibodies for treating neoplastic cells by administration of a therapeutically effective amount of an anti-neoplastic therapeutic agent conjugated to such a monoclonal antibody.

The present invention also relates to a method of treating neoplastic cells comprising administration of a therapeutically effective amount of a neoplastic therapeutic agent conjugated to a binding fragment of a monoclonal antibody of the present invention.

Another aspect of the present invention relates to a method of determining the presence of SCF receptors in a cell sample comprising the steps of:
(a) exposing a cell sample to a monoclonal antibody of the present invention;
(b) detecting the binding of said monoclonal antibody to SCF receptors.

The monoclonal antibodies of the present invention are also useful as a method of modifying sensitivity to cell cycle-specific chemotherapeutic agents comprising administration of a SCF-inhibiting amount of a monoclonal antibody of the present invention.

DETAILED DESCRIPTION OF THE INVENTION

Figure 1:
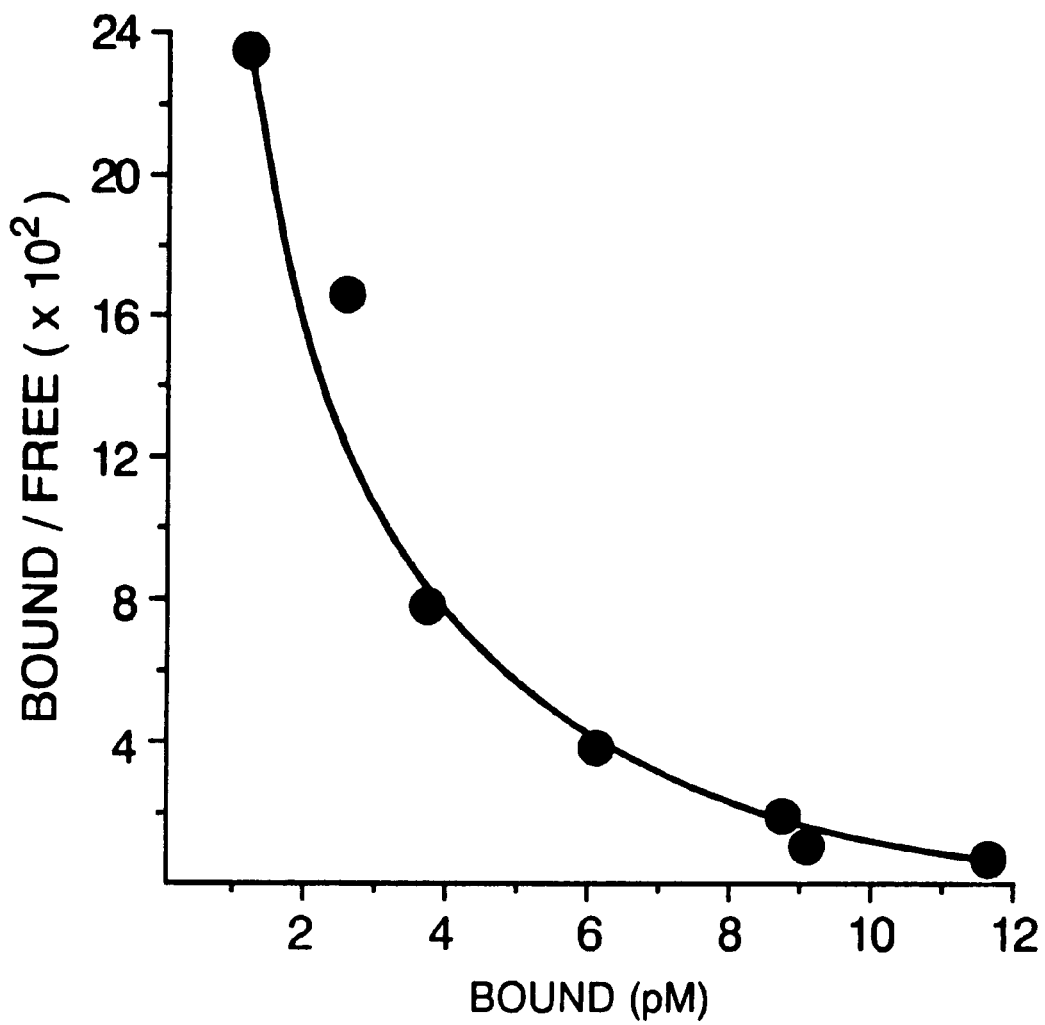
FIG. 1: Scatchard analysis of $^{125}$IhSCF binding to human fetal liver cells. $0.9 \times 10^6$ fetal liver cells were incubated with $^{125}$IhSCF (5 picomolar to 2 nanomolar) and 100 fold excess unlabelled hSCF for 4 hours at 15° C.

The present invention relates to a monoclonal antibody comprising a monoclonal antibody having an ability to bind to an SCF receptor. Preferably, the binding of the monoclonal antibody to the SCF receptor will also inhibit binding of an SCF molecule to said SCF receptor. Preferably, the SCF and the SCF receptor will be of human origin. More preferably, the monoclonal antibody will be of the IgG2a isotype.

Such a monoclonal antibody can be obtained by general methods, including the steps of immunizing or sensitizing an animal with an antigen or immunogen, obtaining the antibody-producing cells resulting therefrom, fusing such antibody producing cells to a stable and long living cell line (an immortal cell line) to produce hybridomas, screening the hybridomas to select a colony consisting of cells that produce the desired antibody, and isolating the resulting monoclonal antibody from such cells.

Sensitization can be accomplished by injecting the antigen into an antibody producing species. Preferably the injection will be into a mammal and more preferably into mice. Usually an initial injection is given followed by subsequent booster injections to maximize the response. Optimally, the injection regime is in multiple doses given to Balb/C mice, e.g., one injection intraperitoneally per week for three consecutive weeks. The amount of antigen injected must be adequate to elicit a sufficient amount of antibody to be detectable. Preferred amounts of antigen to be injected are $10^4$ to $10^8$ cells containing SCF receptors, preferably $10^5$ to $10^7$ cells containing SCF receptors, most preferably about $10^6$ cells containing SCF receptors.

In addition, the generation of human monoclonal antibodies can be performed using in vitro immunization techniques [Ho et al., J. Immunol. 135:3831 (1985)]. The variable region of the mouse monoclonal antibody can also be genetically engineered onto the constant region of a human immunoglobulin which may be preferable for use in humans to prevent problems of immunogenicity often associated with administration of foreign proteins to humans.

These so called "chimeric antibodies" can be obtained by splicing genes encoding the variable antigen-binding regions of a human antibody molecule to the constant regions of a human antibody molecule [Sahagan et al., J. Immunol. 137:106601074 (1986); Beidler et al., J. Immunol. 141:4053–4060 (1988); Morrison et al., Ann. N.Y. Acad. Sci. 507:187–198 (1988)].

A further refinement envisioned within the present invention is production of chimeric antibodies containing a murine hypervariable region coupled to human constant and framework variable regions [Reichman et al., Nature 332:323–327 (1988)]. Most antigen specificity resides in defined segments of the V regions (hypervariable regions) or CDR regions (complementary-determining regions). Antigen-combining sites are formed by CDR loops extending from the remaining framework portions of the V regions. Host immune responses may be generated against the less variable rodent framework V regions of chimeric antibodies. Chimeric antibodies containing human framework V regions retain the antigen binding specificity conferred by the murine CDR regions but are unlikely to elicit a host immune response. Total gene synthesis is the most practical method of preparing CDR-replaced variants in which CDRs from a rodent antibody are transplanted into a human framework. Following sequencing of the desired V region, the sequence is chemically synthesized, cloned, and then inserted into an appropriate expression vector.

The antigens that are useful in producing the monoclonal antibodies of the present invention are any cell line that displays an SCF receptor on its surface. Such cell lines include the human erythroleukemia cell lines OCIM1 [Papayannopoulou et al., Blood 72:1029–1038 (1988)], K562 (ATCC CCL 243); the myeloid or monocytic cell lines KG1 (ATCC CCL 246), KG1α (ATCC CCL 246.1), AML-193 [Santoli et al., J. Immunology 139:3348, (1987)], U937 (ATCC CRL 1593); the lymphoid cell lines Daudi (ATCC CCL 213), IM-9 (ATCC CCL159); mast cell line HMC-1, [Butterfield et al., Leukemia Research 12:345 (1988)]; bladder carcinoma cell lines 5637 (ATCC HTB9), COS (ATCC CRL 1650), BHK (ATCC CCL 10); the gastric carcinoma cell line KAT03 (ATCC HTB103); the small cell carcinoma lines H69 (ATCC HTB 119), H128 (ATCC HTB 120); and the breast carcinoma cell line DU4475 (ATCC HTB 123), which have been deposited with the American Type Culture Collection, 10801 University Boulevard, Manassas, Va. 20110-2209. Preferred antigens are the human erythroleukemia cell line OCIM1.

As a result of the sensitization process, the sensitized animal will produce B-cells that produce and secrete antibodies specific for the antigen. Such cells can be isolated for further use by removing the spleen of the immunized mouse.

The antibody producing cells thus obtained can then be fused to a suitable stable and long living cell line (immortal cell line) using techniques that are known in the art [Kohler and Milstein, Nature 256:495–497 (1975)]. Suitable cell lines for fusion to the antibody producing cells are any cell line that lacks the ability to synthesize antibodies, preferably also lacking in the ability to grow on medium containing a selection agent, most preferably possessing the mutant hypoxanthine-guanidine phosphoribosyl transferase gene (HGPRT- gene), which cannot produce the active hypoxanthine-guanidine phosphoribosyl transferase protein. Hypoxanthine-guanidine phosphoribosyl transferase is necessary to grow on a medium containing aminopterin. Such cell lines that are preferred include myeloma cells, more preferably the NS-1 murine myeloma cell line [ATCC T1B 18; Nowinski et al., Virology 93:111–126 (1979)]. Recently, there has even been success in using human cell lines as fusion partners [Banchereau et al., Science 251:70–72 (1991)].

The resulting fusion partners can then be screened to select a colony consisting of cells that produce the desired antibody. Screening techniques are known in the art, and usually involve the growing of the fused cells on a medium containing a selection agent that (1) would lead to the death of the unfused immortal cells when such immortal cells lack the ability to circumvent the selection agent but (2) allow growth of cells containing genetic material from the antibody producing cell when such genetic material contains the potential to circumvent the selection agent. A preferred immortal cell line contains the HGPRT- gene and a preferred medium contains aminopterin, more preferably the medium hypoxanthine aminopterin thymidine (HAT). As a result, only the fusion cells having both the HGPRT+ gene from the antibody producing cell line and the characteristic of immortality from the immortal cell line would survive and grow in the medium.

The successful fusion cells, or hybridomas, can then be screened to determine if they have the ability to produce antibodies to the antigen used for sensitization. In the case of SCF, such screening can be by the ability of the hybridoma products to bind to SCF receptors, the ability of the hybridoma products to inhibit binding of SCF to SCF receptors, or by standard immunological techniques (e.g., immunoprecipitation of radiolabelled purified SCF receptor) or by ability of the hybridoma products to recognize purified SCF receptor in an ELISA assay. Preferably, the hybridomas can be screened by the ability of hybridoma products to block binding of SCF to SCF receptors.

Stem cell factors (SCFs) useful in these assays include any of the SCFs from various species. Such SCFs are usually in solution with a suitable adjuvant, which adjuvant may contain buffers, salts, etc. Preferably, the SCF will be a human SCF (HuSCF), more preferably a recombinant human SCF (rHuSCF), and most preferably a rHuSCF produced in E. coli. Such SCFs can be obtained as previously described [Zsebo et al., Cell 63:195–212 (1990); and co-pending U.S. patent application Ser. Nos. 07/589,701, 07/573,616, and 07/537,198, filed Oct. 1, 1990, Aug. 24, 1990, and Jun. 11, 1990, respectively, all of which are hereby incorporated by reference for their relevant teachings].

Those hybridomas that are positive for secretion of antibodies to the SCF receptor can then be subcloned and essentially maintained indefinitely. Such selected hybridomas can also be cultured for the production of the monoclonal antibodies that they secrete. The desired monoclonal antibody can be isolated from a culture of such hybridomas using techniques that are known in the art, including protein A-sepharose column chromatography [Ey et al., Immunochemistry 15:429 (1978)].

The preferred monoclonal antibodies of the present invention are those designated SR-1, deposited as BA7.3C.9 with the American Type Culture Collection, 10801 University Boulevard, Manassas, Va. 20110-2209 U.S.A. on Apr. 4 , 1991, and given the Accession Number HB10716.

The monoclonal antibodies of the present invention can be used in a method of purifying hematopoietic cells comprising the steps of:
  (a) exposing a mixture of cells to such monoclonal antibodies;
  (b) separating cells that bind to said monoclonal antibodies from cells that do not bind to said monoclonal antibodies.

The exposure of a cell mixture to such monoclonal antibodies can be in solution, as is the case with fluorescence-activated cell sorting, or it can be with the monoclonal antibody immobilized on a solid support, such as is the case with column chromatography or direct immune adherence. In addition, a combination of soluble and solid support monoclonal antibodies can be used to expose the cell mixture to such monoclonal antibodies, as has been the case with anti-CD34 antibody and a biotinylated second antibody put through an avidin column to remove breast cancer cells in human transplants [Bensinger et al., J. Clin. Apheresis 5:74–76 (1990); Berenson et al., Blood 76:509–515 (1986)].

The mixture of cells that is to be exposed to the monoclonal antibody can be any solution of bone marrow cells, blood-cells or tissue cells. Preferably, the cell mixture is from mammalian bone marrow, circulating blood, or suspected tumor tissue. After exposure of the cell mixture to the monoclonal antibody, those cells with SCF receptors will bind to the monoclonal antibody to form an antibody-SCF-receptor-cell complex. Such SCF receptor cell complexes can then be separated from noncomplexed cells by methods that are known in the art. Preferred methods of separation include column chromatography, fluorescence-activated cell sorting, magnetic bead separation, and direct immune adherence.

The hematopoietic cells thus purified can be employed in a method of reconstituting hematopoietic cells comprising bone marrow transplantation. Methods of bone marrow transplantation are known in the art [Hill et al., Bone Marrow Transplant. 4:69–74 (1989)], but heretofore it has not been possible to use such a homogeneous population of cells having SCF receptors as the material transplanted. Such cells are responsible for long term engraftment in a bone marrow transplant and can be separated from contaminating tumor cells that may be present in the bone marrow using the methods described above. Moreover, the cells having SCF receptors purified by the purification method of the present invention can be further subfractionated to obtain even more homogeneous cell populations. For example, a population of SCF-receptor-containing cells can be sequentially exposed to monoclonal antibodies specific for other cell surface proteins that occur on only certain subpopulations of the SCF-receptor-containing cells. Examples of other monoclonal antibodies that can be used in such a sequential method of purification include monoclonal antibodies to the CD34 antigen which is also expressed on hematopoietic stem cells [Andrews et al., J. Exp. Med. 169:1721–1731 (1989); Civin, U.S. Pat. No. 4,965,204, issued Oct. 23, 1990; Civin, European Patent Application 395355, published Oct. 31, 1990].

Hematopoietic cells purified according to the present invention can also be used in a method of gene therapy comprising retrovirally-mediated gene transfer into the purified cells. Methods of retrovirally-mediated gene transfer are known in the art [Bodine et al., Proc. Natl. Acad. Sci. USA 86:8897–8901 (1989)], but heretofore it has not been possible to use such a homogeneous population of cells having SCF receptors as the cells transfected. Such transfected cells can then be used in bone marrow transplantation.

The present invention also relates to a method of separating normal cells from neoplastic cells comprising the steps of:
  (a) exposing a mixture of cells comprising normal cells and neoplastic cells to a monoclonal antibody according to the present invention;
  (b) separating normal cells from neoplastic leukemia cells based upon a differential in numbers of SCF receptors on normal cells and neoplastic leukemia cells. The bone marrow cells can be labelled with the monoclonal antibodies of the present invention, then with a biotinylated goat anti-mouse antibody and passed through an avidin column. This approach can be used to positively or negatively select cells; cells with higher numbers of SCF receptors will be retained by the column while cells with lower SCF receptor display will pass through the column. Alternatively, a method for separating cells with high and low SCF receptor display is direct immune adherence and fluorescence-activated cell sorting. With fluorescence-activated cell sorting (FACS), cells displaying SCF receptors can be mixed with monoclonal antibodies specific for SCF receptors. The monoclonal antibodies are (1) conjugated with a fluorescence agent such as fluoresceine isothiocyanate (FITC) or phycoerythrin (PE); (2) conjugated with a first biological molecule (e.g., biotin) and mixed with a second biological molecule that specifically binds to the first biological molecule (e.g., avidin or streptavidin), the second biological molecule being conjugated with a fluorescent agent such as FITC or PE; or (3) further mixed with a second antibody specific for the species of antibody of the anti-SCF receptor monoclonal antibody (e.g., a goat or sheep anti-mouse antibody), the second antibody being conjugated with a fluorescent agent such as FITC or PE. Such fluorescently labelled cells can then be sorted using standard technology according to the level of fluorescence exhibited by the cells.

The monoclonal antibodies of the present invention can also be useful in treating neoplastic cells by administration of a therapeutically effective amount of an anti-neoplastic therapeutic agent conjugated to such a monoclonal antibody. A therapeutically effective amount of a neoplastic therapeutic agent is any amount of a compound that will cause inhibition of growth and/or development of neoplastic cells, preferably causing death of the cell and a decrease in the total number of neoplastic cells in an organism. Examples of such neoplastic therapeutic agents include antibodies coupled to the radioisotope $^{125}$I [Press et al., *J. Clin. Oncol.* 07:1027–1038 (1989)] or to toxin conjugates such as ricin [Uhr et al., *Prog. Clin. Biol. Res.* 288:403–412 (1989)] and the diptheria toxin [Moolten, *J. Natl. Con. Inst.* 55:473–477 (1975)].

Conjugation of the leukemia therapeutic agent to the monoclonal antibody can be accomplished using known techniques as described above [Press et al., *J. Clin. Oncol.* 7:1027–1038 (1989); Uhr et al., *Prog. Clin. Biol. Res.* 288:403–412 (1989)]. Preferably, the conjugation site on the monoclonal antibody is at a location distinct from the binding site for the monoclonal antibody to the SCF receptor. It is also preferred that the conjugation site on the neoplastic therapeutic agent be at a functional group distinct from the active site of the therapeutic agent. More preferably, the conjugation site will also be situated so as to minimize conformational changes of the monoclonal antibody or the neoplastic therapeutic agent.

The present invention also relates to a method of treating neoplastic cells comprising administration of a therapeutically effective amount of a neoplastic therapeutic agent conjugated to a binding fragment of a monoclonal antibody of the present invention. Suitable binding fragments are those fragments that retain sufficient size and structure to allow binding of the fragment to the SCF receptor. Such fragments can be prepared by numerous methods, including proteolytic digestion [Garvey et al., *Methods in Immunology*, Chapter 31, W. A. Benjamin, Reading, Mass. (1977)]. The prepared binding fragments can be assayed for ability to bind to the SCF receptor using the binding assays previously described.

Another use of the monoclonal antibodies of the present invention relates to a method of determining the presence of SCF receptors in a cell sample comprising the steps of:

(a) exposing a cell sample to a monoclonal antibody of the present invention;

(b) detecting the binding of said monoclonal antibody to SCF receptors.

The exposure of a cell mixture to such monoclonal antibodies can be in solution, as is the case for fluorescence-activated cell sorting, or it can be on solid tissue specimens such as biopsy material, or it can be with the monoclonal antibody immobilized on a solid support, as is the case with column chromatography or direct immune adherence. The mixture of cells that is to be exposed to the monoclonal antibody can be any solution of blood cells or tissue cells. Preferably, the cell mixture is from normal mammalian cells, mammalian bone marrow, circulating blood, or suspected tumor tissue, more preferably normal cells, leukemia cells and solid tumor cells. After exposure of the cell mixture to the monoclonal antibody, those cells with SCF receptors will bind to the monoclonal antibody to form an antibody-SCF-receptor complex. The presence of the antibody-SCF-receptor complex, and therefore SCF receptors, can be detected by methods known in the art. These methods include ELISA, immunohistochemistry, and autoradiography using $^{125}$C-labelled Staph Protein A.

The monoclonal antibodies of the present invention are also useful as a method of modifying sensitivity to cell cycle-specific chemotherapeutic agents comprising administration of a SCF-inhibiting amount of a monoclonal antibody of the present invention. An SCF-inhibiting amount of a monoclonal antibody is sufficient quantities of monoclonal antibody to significantly inhibit the binding of SCF to its receptor or to significantly decrease the growth and development of cells containing the SCF receptor, e.g., early pluripotent hematopoietic progenitors, leukemia cells, solid tumor cells, bone marrow cells. Generally, a significant inhibition is inhibition that is larger than the variance due to error expected with a given method of measuring the inhibition. Preferably, the inhibition will decrease binding of SCF to its receptor by at least 50%, more preferably by at least 75%, more preferably by at least 90%, and most preferably inhibition will decrease binding of SCF to its receptor essentially entirely. Generally, a significant decrease of the growth and/or development of cells containing the SCF receptor is a decrease larger than the variance due to error expected with a given method of measuring the growth and/or development. Preferably, decrease of the growth and/or development of cells containing the SCF receptor is a lowering of the growth rate of SCF-receptor-containing cells, preferably a decrease to at least one-half, more preferably to at least one-tenth, and most preferably to at least one-hundredth.

Administration of the monoclonal antibodies of the present invention involves administration of an appropriate amount of a pharmaceutical composition containing the monoclonal antibodies as an active in ingredient. In addition to the active ingredient, the pharmaceutical composition may also include appropriate buffers, diluents and additives. Appropriate buffers include Tris-HCl, acetate, glycine and phosphate, preferably phosphate at pH 6.5 to 7.5. Appropriate diluents include sterile aqueous solutions adjusted to isotonicity with NaCl, lactose or mannitol, preferably NaCl. Appropriate additives include albumin or helatin to prevent adsorption to surfaces, detergents (e.g., Tween 20, Tween 80, Pluronic F68), solubilizing agents (e.g., glycerol, plyethylene glycol), antioxidants (e.g., ascorbic acid, sodium metabisulfite) and preservatives (e.g., Thimersol, benzyl alcohol, parabens). A preferred additive is Tween 80.

Administration may be by any conventional means including intravenously, subcutaneously, or intramuscularly. The preferred route of administration is intravenous. Administration may be a single dose or may occur in an appropriate number of divided doses.

Preferably, the pharmaceutical preparation is in unit dosage form. In such form, the preparation is subdivided into unit doses containing the appropriate quantities of the active component, e.g., an effective amount to achieve the desired purpose.

The actual dosage employed may be varied depending upon the requirements of the patient and the severity of the condition being treated. Determination of the proper dosage for a particular situation is within the skill of the art.

Generally, treatment is initiated with smaller dosages which are less than the optimum dose of the compound. Thereafter, the dosage is increased by small increments until the optimum effect under the circumstances is reached. For convenience, the total daily dosage may be divided and administered essentially continuously or in portions during the day if desired. The amount and frequency of administration will be regulated according to the judgment of the attending clinician considering such factors as age, condition and size of the patient as well as severity of the disease being treated.

A typical recommended dosage regime for use in the present invention is from about 0.1 to about 10 mg active ingredient per kg body weight per day.

EXAMPLES

The following examples are intended to illustrate specific embodiments of the present invention without limiting the scope thereof. All references cited are hereby incorporated by reference for their relevant teachings.

Example 1

Sensitization of Animals

Appropriate antigens for use in sensitization were any cell displaying SCF receptors. The presence of SCF receptors was determined using radiolabelled SCF. Human and rodent $SCF^{164-165}$ was obtained according to the methods of Zsebo et al., Cell 63:195–212 (1990); and PCT application No. US90/05548, filed Sep. 28, 1990, application Ser. Nos. 07/589,701, 07/573,616, and 07/537,198, filed Oct. 1, 1990, Aug. 24, 1990, and Jun. 11, 1990, respectively. These SCFs were labelled with $^{125}I$ using the chloramine-T method of Hunter and Greenwood [Nature 194:495–496 (1962)]. The specific activity of the $^{125}I$ human SCF (hSCF) varied from 2,000 to 2,500 Ci/mmol. Both $^{125}I$ hSCF and $^{125}I$ rat SCF (rSCF) retained the ability to bind to SCF-receptor-containing cells. Moreover, self displacement analysis [Calvo et al., Biochem. J. 212:259–264 (1983)] with $^{125}IhSCF$ and unlabelled hSCF demonstrated that the binding affinity was not altered by iodination. A number of other hematopoietic growth factors were tested for binding to the erythroleukemia cell line OCIM1 [Papayannopoulou et al., Blood 72:1029–1038 (1988)]. Table 1 shows that a 100-fold molar excess of unlabelled hSCF competed very effectively for binding, while a variety of other growth factors did not.

TABLE 1

| COMPETITION WITH $^{125}IhSCF$ FOR BINDING TO OCIM1 CELLS[a] | |
|---|---|
| Competitor | CPM Bound |
| NONE | 1725 |
| SCF | 10 |
| IL-3 | 1830 |
| GM-CSF | 1742 |
| ERYTHROPOIETIN | 1775 |
| G-CSF | 1843 |
| IL-6 | 1693 |

[a]OCIM1 cells were incubated with 200 picomolar $^{125}I$ hSCF with or without a 100 fold excess of the growth factors indicated.

Numerous normal hematopoietic cells, hematopoietic cell lines and neoplastic nonhematopoietic cells were screened for expression of SCF receptors. Normal human marrow mononuclear cells bind hSCF, as do human fetal liver early erythroblasts. Adult late erythroblasts, which were obtained by culturing peripheral blood BFU-E and plucking individual colonies after 14 days, also displayed SCF receptors. Distribution of SCF receptors on normal human marrow cells were determined by autoradiography [Nicola and Metcalf, J. Cell Physiol. 124:313–321 (1985)]. Large cells with high nuclear/cytoplasmic ratio that appeared to be blasts and promyelocytes were densely labelled with approximately 50 to 200 grains per cell. Megakaryocytes also showed $^{125}I$ binding.

A number of human hematopoietic cell lines displayed SCF receptors. The erythroleukemia cell lines OCIM1 and K562 bind SCF, as do the myeloid of monocytic cell lines KG-1, KG1a, AML-193 and U937. The lymphoid cell lines Daudi and IM-9 and the mast cell line HMC-1 all bound SCF. SCF receptors were also found on nonhematopoietic cell lines including the bladder carcinoma line 5367, COS, BHK, the gastric carcinoma cell line KATO3, the small cell carcinoma cell lines H69 and H128, and the breast carcinoma cell line DU475.

SCF receptors were quantitated on normal human fetal liver cells and examined for their response to SCF in colony assays. Human fetal liver cells (gestational age 55 to 80 days) were obtained from therapeutic abortions. Consent was obtained for the use of these tissues, and the studies were approved by the Institutional Review Board at the University of Washington. The cells were incubated with $^{125}IhSCF$ (5 picomolar to 2 nanomolar) ± a 100 fold excess of unlabelled SCF for 4 hours at 15° C. in the presence of metabolic inhibitors. Under these conditions, the equilibrium binding for SCF is achieved and internalization is minimal (<17%). At the conclusion of the incubation period, cell-associated $^{125}IhSCF$ was separated from free $^{125}IhSCF$ by sedimenting the cells through phthalate oil, as described in Broudy et al., Blood 75:1622–1626 (1990). Equations for 1 or 2 classes of receptors were fitted to the data using a ligand program [Munson and Rodbard, Analyt. Biochem. 107:220–239 (1980)]. The human fetal liver cells were found to express 2 classes of SCF receptors as shown in FIG. 1. The high affinity receptor had a Kd of 14 picomolar and the low affinity receptor had a Kd of 2.7 nanomolar with approximately 1,700 receptors/cell.

Figure 2:
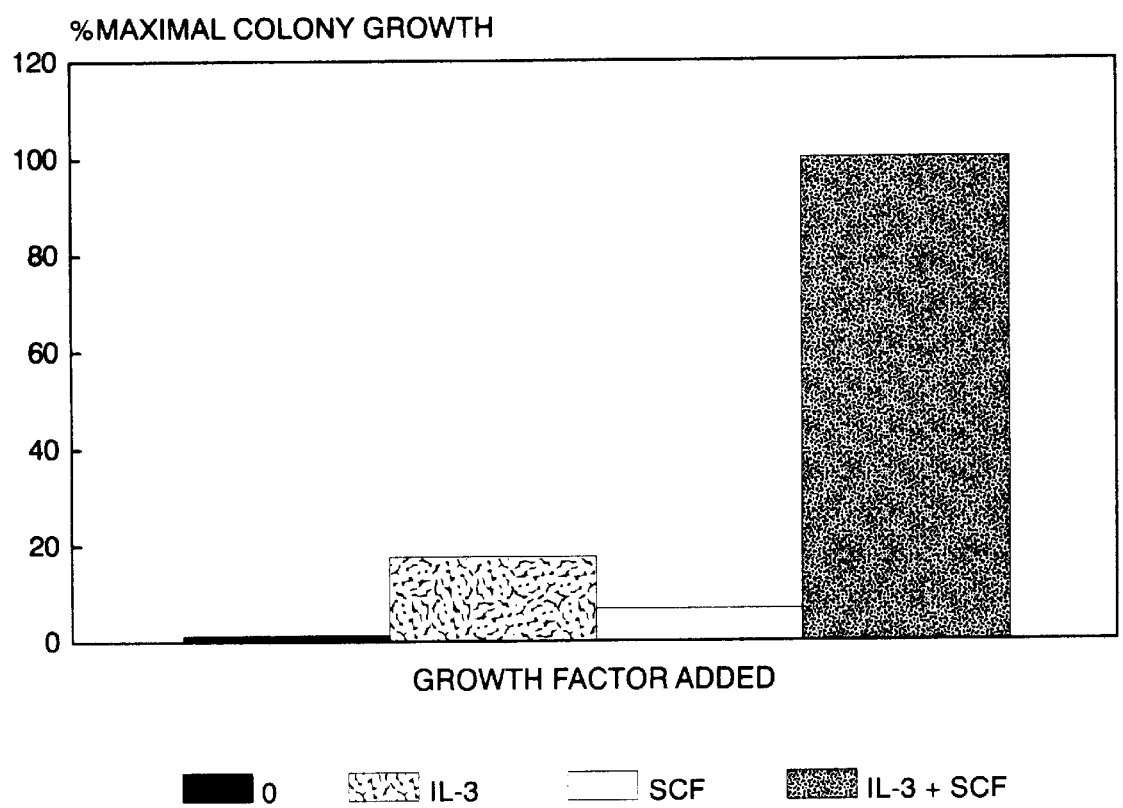
FIG. 2: Effect of recombinant human SCF (rHuSCF) on the growth of acute nonlymphocytic leukemia cells when administered alone or in combination with other growth factors such as interleukin-3.
Figure 3:
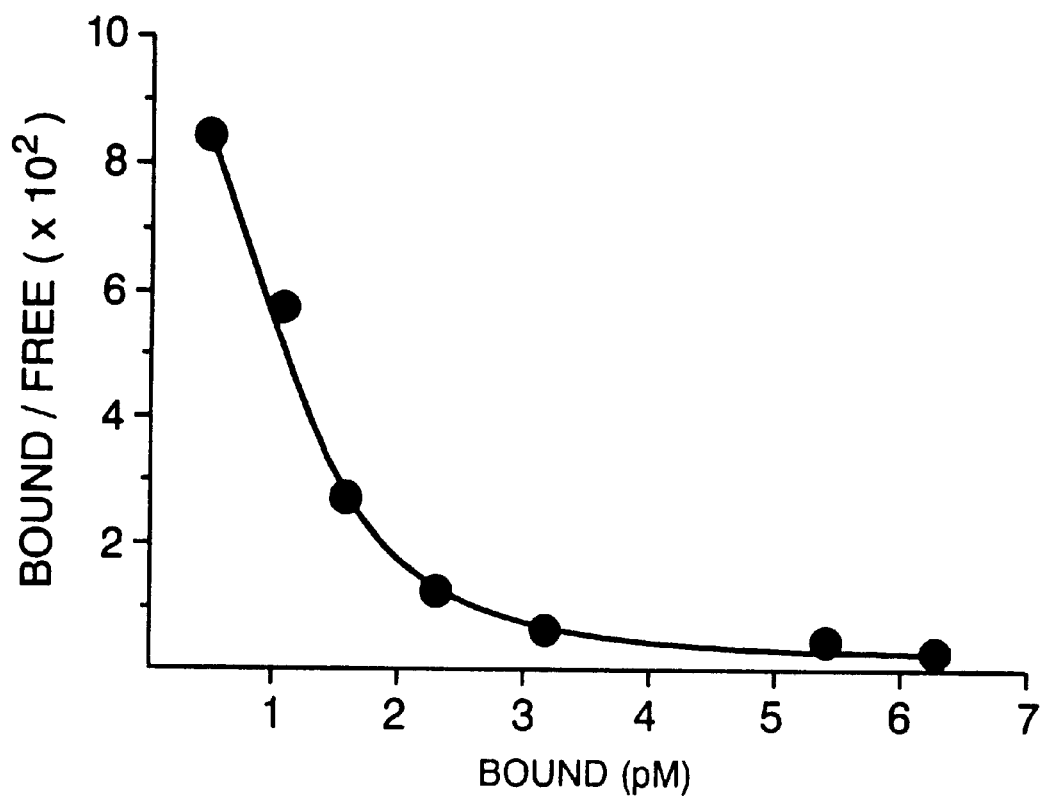
FIG. 3: Scatchard plot of $^{125}$IhSCF binding to blasts from a patient with acute nonlymphocytic leukemia (ANLL).

Neoplastic hematopoietic cells were investigated to determine whether they would also respond to SCF and display SCF receptors. Marrow mononuclear cells from 20 different patients with acute nonlymphocytic leukemia (ANLL) at first presentation and two normal adults were studied. The cells were cultured in agar supplemented with 15% fetal calf serum and recombinant human IL-3. Colonies (>40 cells) and clusters (<40 cells) were counted after 8, 15, and 21 days. SCF receptors were quantified by equilibrium binding studies with $^{125}IhSCF$ ± a 100 fold excess of unlabelled hSCF. The cellular distribution of SCF receptors was examined by autoradiography. SCF stimulated colony growth from 7 of the 20 ANLL marrows studied and from both of the normal marrows. SCF alone had little effect on colony growth, but acted synergistically with IL-3 to increase both the number and size of colonies (FIG. 2). Receptors for SCF were identified on the blasts of all 20 ANLL patients. Ten of the 20 ANLL patients exhibited 2 classes of SCF receptors on their marrow blasts. A Scatchard plot of $^{125}IhSCF$ binding to the blasts from one of the ANLL patients shows approximately 500 high affinity SCF receptors (Kd 16 picomolar) and 7000 low affinity receptors (Kd 7.6 nanomolar) per cell as illustrated in FIG. 3. These binding affinities are similar to those found on normal human fetal liver cells and normal human marrow mononuclear cells. Six of the 20 patients showed a single class of high affinity receptors, while the remaining patients showed a single low affinity binding site. Neither the number of receptors/cell nor the presence of 1 or 2 classes of receptors correlated with growth response to SCF, as has been observed for IL-3, GM-CSF and G-CSF receptors on human ANLL blasts [Park et al., *Blood* 74:56–65 (1989)].

The marrow mononuclear cells from these leukemic patients were greater than 90% blasts while marrow mononuclear cells from normal adults contain a much lower fraction of blasts. The vast difference in the percentage of blasts suggests that it is not accurate to compare the average number of receptors per cell on normal and leukemic marrow samples. Autoradiography, which permits analysis of binding to individual cells, can more accurately be used to compare SCF binding to normal and leukemic blasts. Autoradiographic analysis of $^{125}$IhSCF binding to normal human marrow mononuclear cells on 8 of the ANLL marrow samples was carried out in a single experiment to permit direct comparison. Grain counts indicated that the normal marrow blasts displayed approximately 50 to 200 grains/blast, while the leukemic blasts exhibited from 2 to 20 grains/blast. Thus binding of SCF to leukemic blasts was substantially lower than binding of SCF to normal blasts.

Figure 4:
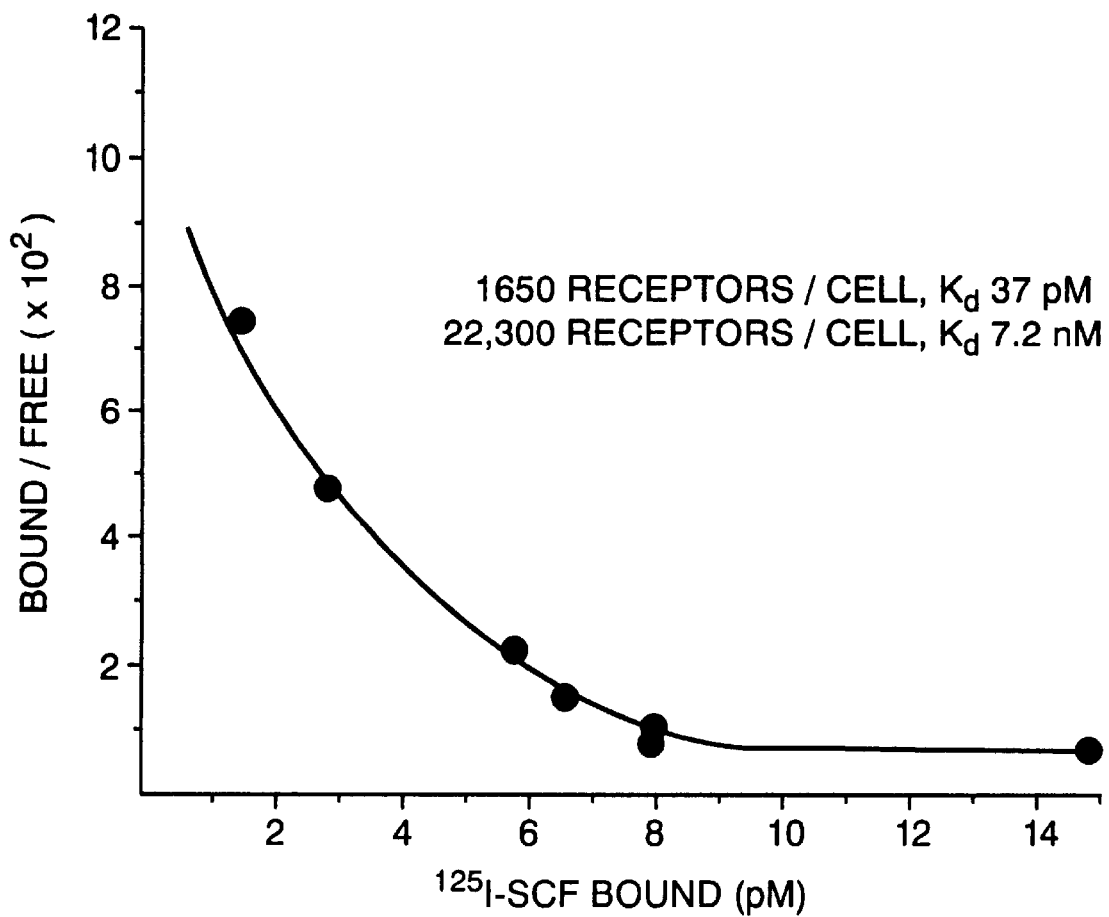
FIG. 4: Scatchard analysis of $^{125}$IhSCF binding to human small cell lung cancer cells. $0.2 \times 10^6$ small cell lung cancer cells (H69 cell line) were incubated with $^{125}$IhSCF (5 picomolar to 2 nanomolar) and 100 fold excess unlabelled hSCF for 4 hours at 15° C.

SCF receptors were also found on tumor cell lines of non-hematopoietic origin including H69, H128, and DU475. A Scatchard plot of $^{125}$IhSCF binding to H69 cells (FIG. 4) shows 1650 high affinity receptors per cell (Kd 37 picomolar) and 22,300 receptors per cell (Kd 7.2 nanomolar).

Figure 5:
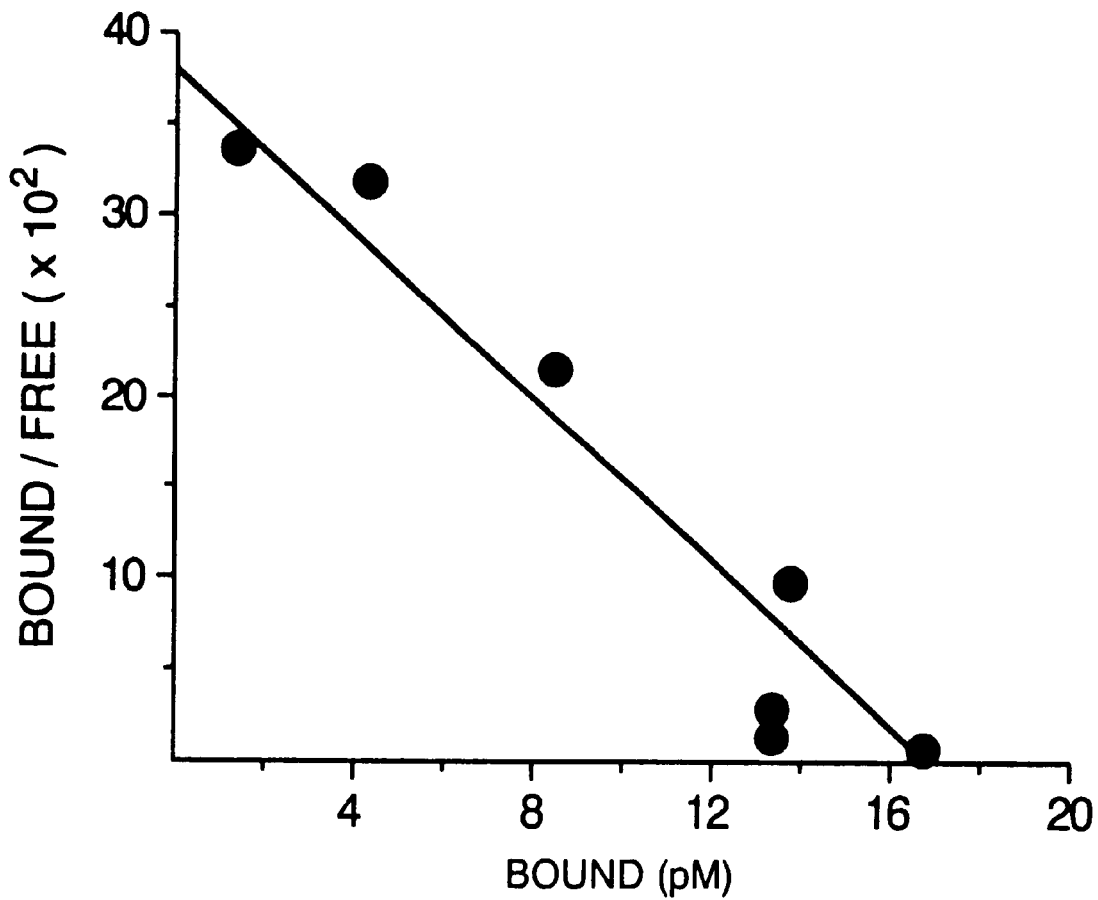
FIG. 5: Scatchard plot of $^{125}$IhSCF binding to OCIM1 cells.

OCIM1 is a human erythroleukemia cell line that displays receptors for erythropoietin [Broudy et al., *Proc. Natl. Acad. Sci. USA* 85:6513–6517 (1988)], GM-CSF, and IL-3. Equilibrium binding studies with $^{125}$IhSCF showed that OCIM1 cells display about 200,000 SCF receptors per cell as shown in FIG. 5. A single class of high affinity SCF receptors (Kd 45 picomolar) is evident. hSCF did not stimulate the growth of OCIM1 cells in suspension culture. MB-02 is a growth factor dependent human erythroleukemia cell line that will undergo erythroid differentiation in the presence of erythropoietin [Perrine et al., *Biochem. Biophys. Res. Comm.* 164:857–862 (1989)]. MB-02 cells respond to hSCF with proliferation, but not erythroid differentiation, and display both high and low affinity SCF receptors.

The OCIM1 cells were used as an immunogen because of their high SCF receptor display, although any cell displaying SCF receptors could be used as an immunogen to elicit antibodies to the SCF receptor.

Eight week old female Balb/C mice were injected intraperitoneally with 10$^6$ OCIM1 cells on three occasions at one week intervals.

Example 2

Production of Monoclonal Antibody to SCF Receptor

Five days following the third injection, the spleen was removed and splenic cells were fused with NS-1 murine myeloma cells [Nowinski et al., *Virology* 93:111–126 (1979)]. The supernatants from a total of 288 hybridoma wells were screened for the ability to block binding of $^{125}$IhSCF to OCIM1 cells as described in Example 5, below. A positive hybridoma was identified, cloned and grown as an ascites-producing tumor in pristane-primed Balb/C mice. The antibody was identified as IgG2a and was named SR-1 (deposited as BA7.3C.9 with the American Type Culture Collection, 10801 University Boulevard, Manassas, Va. 20110-2209 U.S.A. on Apr. 4, 1991 and given the ATCC Accession Number HB10716. Screening of additional hybridomas should lead to the identification of additional anti-SCF receptor monoclonal antibodies at a similar frequency.

Example 3

Production of Chimeric Monoclonal Antibodies Having Murine Variable Regions and Human Constant Regions Genomic DNA is prepared from the hybridoma cell line producing SR-1 monoclonal antibodies, and functional exons encoding the variable regions of heavy and light chains ($V_H$ and $V_\kappa$, respectively) are identified by DNA restriction maps obtained by Southern analysis. Functional $V_\kappa$ exons result when germline $V_\kappa$ genes are rearranged and joined to the $J_\kappa$ gene segment. Similarly, a functional $V_H$ exon is created when a $V_H$ gene is juxtaposed to the $J_H$ gene segment. Specific DNA probe segments are designed to identify rearranged V-regions genes via unique restriction enzyme sites that distinguish the rearranged genotype from the unrearranged germline DNA sequences [Oi and Morrison, *BioTechniques* 4:214–221 (1986)]. Recombinant DNA techniques are used to construct a genomic DNA library, and the desired V-genes are isolated and sequenced to confirm the identification of rearranged expressed $V_H$ and $V_L$ exons. The $V_H$ exon is inserted into the pSV2ΔHgpt vector [Mulligan and Berg, *Science* 209:1422–1427 (1980); Mulligan and Berg, *Proc. Natl. Acad. Sci. USA* 78:2072–2076 (1981)], which contains an ampicillin resistance gene to maintain the plasmid in *E. coli*, and a mycophenolic acid resistance gene to permit selection in mammalian cells growing in medium containing hypoxanthine, mycophenolic acid and xanthine. The desired $V_\kappa$ exon is inserted into the pSV184ΔHneo vector, which is derived from the pACYC184 plasmid [Chang and Cohen, *J. Bacteriol.* 143:1141–1156 (1978)]. This vector contains a chloramphenicol resistance gene used to maintain the plasmid in *E. coli* and a gentamycin resistance gene used to select for mammalian cells transfected with this plasmid vector. Transcription of the gentamycin resistance gene (neo) is directed by the SV40 early region promoter. Known DNA regulatory sequences for the immunoglobulin heavy and light chains are also included in these transfection vectors [Calame, *Annual Rev. Immunol.* 3:159–196 (1985); Morrison and Oi, *Annual Rev. Immunol.* 2:239–256 (1984)]. Both plasmids are maintained in *E. coli* HB101 [Boyer and Roulland-Dussoix, *J. Mol. Biol.* 41:459 (1969)] grown in chloramphenicol and ampicillin selection medium.

Protoplasts of these bacterial cells, prepared by treatment with lyzozyme and EDTA, are fused via polyethylene glycol treatment or electroporation) with the immunoglobulin non-producing mouse SP2/0 myeloma cell line (ATCC CRL 1581). Transfected SP2/0 cells are isolated using medium containing gentamycin, hypoxanthine, mycophelolic acid and xanthine. The resulting transfectomas are screened for production of mouse:human chimeric SR-1 antibodies using the techniques described in Example 2.

Example 4

Assay to Determine Binding of Monoclonal Antibody SR-1 to SCF Receptor

COS-1 cells were transfected with a vector containing the transmembrane and external domain of human c-kit [Zsebo et al., *Cell* 63:213–224 (1990)], or with the vector alone. Indirect immunofluorescence analysis using SR-1 followed by FITC-conjugated goat anti-mouse IgG showed that SR-1 recognized none of the cells transfected with vector alone and 5 to 10% of the cells transfected with c-kit. This demonstrates that SR-1 binds to c-kit.

Figure 6A:
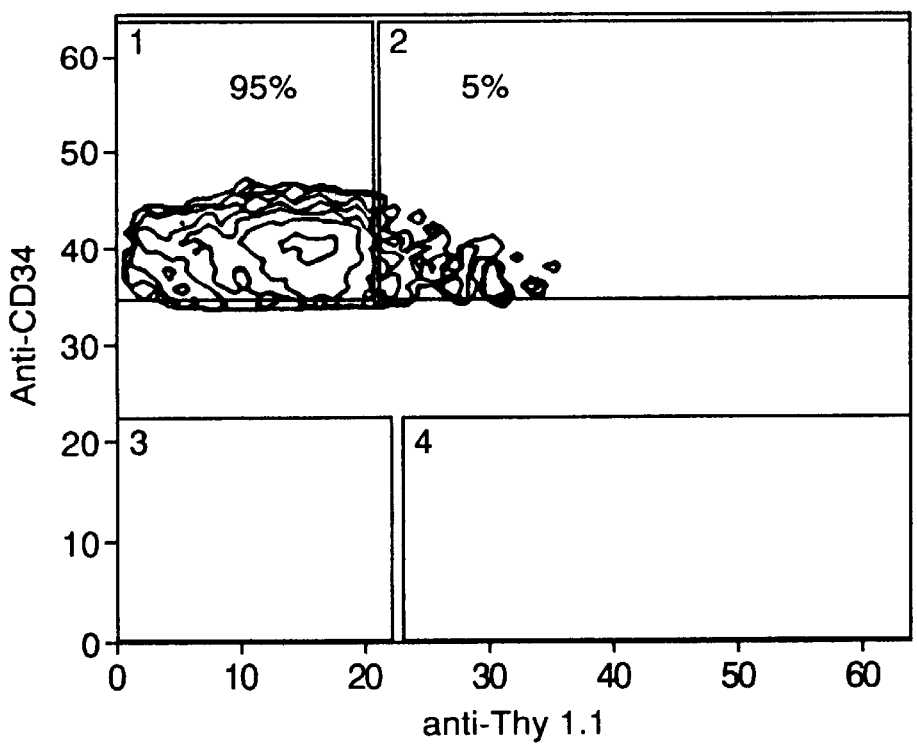
FIG. 6: Indirect immunofluorescence analysis of SCF binding to normal human bone marrow. The bone marrow cells were simultaneously labelled with anti-CD34 monoclonal antibody and with either SR-1 (FIG. 6A) or with an isotype matched control monoclonal antibody (anti-Thy 1.1), (FIG. 6B).
Figure 6B:
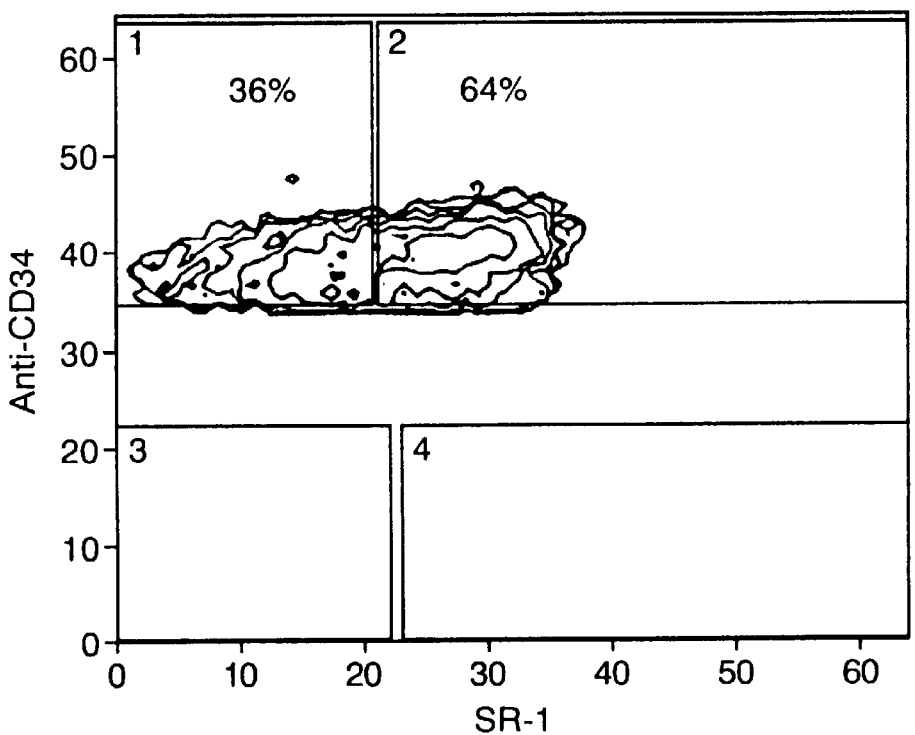

Analysis by indirect immunofluorescence also showed that the monoclonal antibody (SR-1) recognizes a surface epitope present on both OCIM1 cells and a small percentage (2–5%) of marrow mononuclear cells (FIG. 6A). The SR-1 antibody recognizes a portion (50–75%) of the hematopoietic cells that display CD34 (FIG. 6B). These results were obtained when bone marrow cells were simultaneously labelled with anti-CD34 monoclonal antibody (antibody 12.8, Andrews et al., *J. Exp. Med.* 172:355, (1990); Civin, U.S. Pat. No. 4,965,204, issued Oct. 23, 1990; Civin, European Patent Application 395355, published Oct. 31, 1990) and with either SR-1 or with an isotype matched control monoclonal antibody anti-Thy 1.1, Andrews et al., *J. Exp. Med.* 172:355, (1990). These examples demonstrate that SR-1 and indirect immunofluorescence analysis can be used to identify cells that express c-kit. SR-1 antibodies have also been directly conjugated to PE, and this preparation has been used to identify cells that display c-kit. Alternative methods are biotinylation of the SR-1 antibody, with binding of this preparation detected using avidin or streptavidin conjugated to FITC or PE.

Example 5

Assay to Determine Inhibition of SCF Binding to SCF Receptor by Monoclonal Antibody SR-1

Cells that express the SCF receptor were incubated with $^{125}$IhSCF (100 picomolar) with or without varying quantities of SR-1 antibody. Preferably, a dilution of 1:1000 to 1:100,000 of SR-1 ascites is used. At the conclusion of the incubation, cell associated $^{125}$IhSCF was separated from free $^{125}$IhSCF by sedimenting the cells through phthalate oil [Broudy et al., *Blood* 75:1622–1626 (1990)].

The ascites blocks binding of $^{125}$IhSCF to OCIM1 cells at a 1:100,000 dilution (Table 2). This monoclonal antibody is specific for the human SCF receptor in that it does not block binding of $^{125}$I-ratSCF to the murine MC/9 cell line.

TABLE 2

SR-1 BLOCKS BINDING OF $^{125}$I hSCF TO OCIM1 CELLS[a]

| Addition | CPM Bound |
|---|---|
| 0 | 1548 |
| Unlabelled SCF | 89 |
| Ascites 1:1,000 | 70 |
| Ascites 1:10,000 | 39 |
| Ascites 1:100,000 | 118 |
| Ascites 1:1,000,000 | 760 |
| Ascites 1:10,000,000 | 1375 |

[a]OCIM1 cells were incubated with 100 picomolar $^{125}$IhSCF with dilutions of SR-1 ascites fluid.

Figure 7:
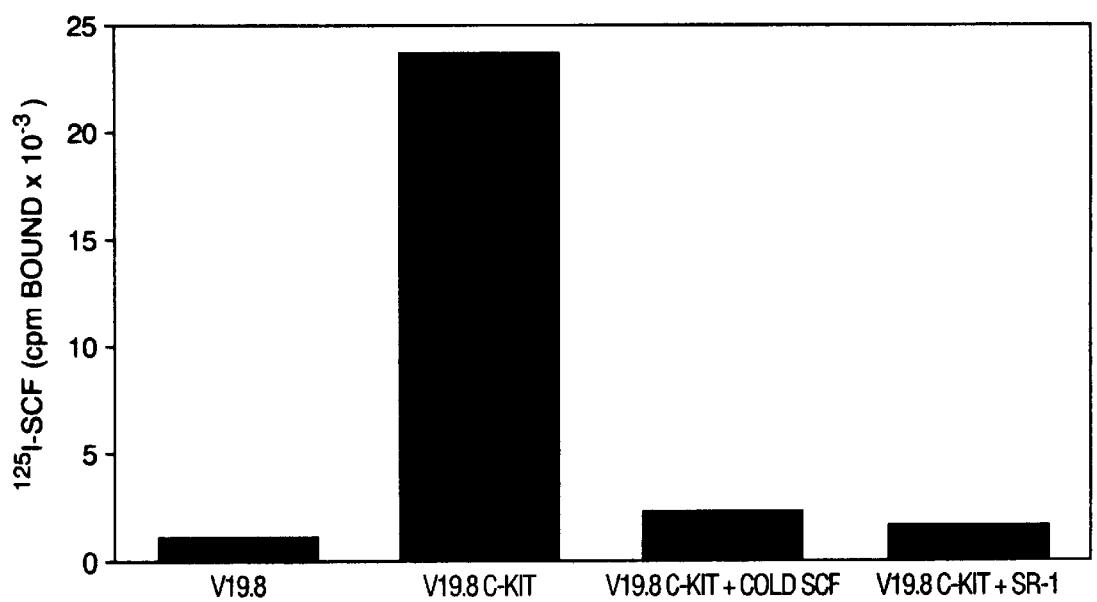
FIG. 7: Recognition of the SCF receptor, c-kit, by monoclonal antibody SR-1. COS-1 cells were transfected with V19.8 or V19.8 containing human c-kit. The COS cell membranes were incubated with 1 nanomolar $^{125}$IhSCF with or without cold SCF or SR-1 ascities (diluted 1:1000) and bound labelled SCF was measured.

COS-1 cells were also transfected with V19.8, Zsebo et al., *Cell 63:213–224* (1990 or V19.8 containing human c-kit. The COS cell membranes were incubated with 1 nanomolar $^{125}$IhSCF with or without cold SCF or SR-1 ascites (diluted 1:1000) and bound labelled SCF measured. SR-1 blocked binding of $^{125}$IhSCF to c-kit as effectively as unlabelled SCF (FIG. 7).

Example 6

SR-1 Neutralizes the Biologic Effect of SCF

In addition to blocking the binding of $^{125}$IhSCF to cells, SR-1 blocks the biologic effects of SCF on colony growth.

SCF stimulates the growth of early erythroid colony forming cells (BFU-E), and SR-1 blocks this effect. SCF does not alter the growth of more mature erythroid colony forming cells (CFU-E) and SR-1 has no effect on CFU-E growth.

Human marrow mononuclear cells were cultured in recombinant human erythropoietin (1 unit/ml, Amgen Inc., Thousand Oaks, Calif.) plus hSCF (50 ng/ml) with or without SR-1 ascites (1:1000 dilution) in semisolid medium. CFU-E were counted on day 7, BFU-E were counted on day 14. Three experiments with duplicate plates were conducted and the results from one such experiment are presented in Table 3.

TABLE 3

EFFECT OF SR-1 ON HUMAN ERYTHROID COLONY GROWTH

| | Colonies/$10^5$ Cells | |
|---|---|---|
| SR-1 ANTIBODY | CFU-E | BFU-E |
| − | 39 | 142 |
| + | 38 | 20 |

Example 7

Conjugation of Monoclonal Antibody SR-1 to a Therapeutic Agent

SR-1 is coupled or conjugated to a variety of agents, for therapeutic and diagnostic use of the resulting conjugates, Scheinberg et al., *Oncology* 1, 31–37 (1987).

For use in in vivo imaging of tumors and tumor masses containing cells expressing c-kit receptor, antibody or antibody fragments are coupled to radioisotopes such as $^{123}$I, $^{131}$I, $^{111}$In, $^{90}$Y, $^{99}$Tc. For use in therapy of such tumors and in therapy of dispersed malignancies such as leukemias, antibody or antibody fragments are coupled to radioisotopes such as $^{32}$P, $^{131}$I, $^{90}$Y, $^{186}$Re, $^{212}$Pb, $^{212}$Bi [Scheinberg et al., *Oncology* 1, 31–37 (1987) and Humm, J. L., *J. Nuclear Medicine* 27, 1490–1497 (1986)]. Conjugation of radioisotopes to antibody is accomplished by direct attachment of radioisotopes to antibody by methods that include pertinning techniques [Schwartz J., *Nuclear Medicine* 28, 721 (1987) and Rhodes et al., *J. Nuclear Medicine* 21, 54 (1980)]; or by way of bifunctional chelate linkers such as those utilizing diethylenetriaminepentaacetic acid (DTPA) [Hnatowich et al., *J. Nuclear Medicine* 26:503–509 (1985)], $N_2S_2$ [Fritzberg et al. *Proc. Natl. Acad. Sciences U.S.A.* 85:4025 (1988)], or macrocyclic chelators [Moi et al., *Cancer Research* (Suppl.) 50:7895–7935 (1990)], which bind both antibody and radioisotope.

For use in therapy, a variety of other toxic agents are attached to antibody. These include antitumor drugs and antibiotics which are toxic by way of interaction with DNA via intercalation (e.g., daunomycin, adriamycin, aclacinomycin) or cleavage of DNA (e.g., esperamycin, calicheamycin, neocarzinostatin), and other toxic cytostatic drugs such as cis-platinum, vinblastine, and methotrexate [Scheinberg et al., *Oncology* 1:31–37 (1987); Greenfield et al., *Antibody, Immunoconjugates, and Radiopharmaceuticals* 4:107–119 (1991); Dillman et al., *Cancer Research* 48:6097–6101 (1988); Hamann et al., *Abstracts of 197th American Chemical Society National Meeting*, Dallas, Tex., U.S.A., Apr. 9–14, 1989, Abstract No. 71A; Y. Sugiura et al., *Proc. Natl. Acad. Sci. U.S.A.* 86:7672–7676 (1989)]. These agents are coupled in ways that include covalent attachment upon reaction with appropriate derivatives of the agents.

Also for use in therapy, many protein and glycoprotein toxins are conjugated to antibody [Blättler et al., *Cancer Cells* 1:50–55 (1989); *Immunotoxins,* Edited by A. E. Frankel Kluwer Academic Publishers, Boston (1988)]. These include bacterial toxins such as Diphtheria toxin, Shigella toxin, and Pseudomonas exotoxin; plant toxins such as ricin, abrin, modeccin, viscumin, pokeweed antiviral protein, saporin, momordin, and gelonin. The toxins contain a catalytic fragment and in some cases fragments or domains that recognize cell surface structures or facilitate translocation across cell membranes. Thus appropriately modified toxins or toxin fragments are used, which permit improved specificity without loss of potency (e.g., modified toxins which themselves lack the capability for cell surface recognition, so that such recognition is provided only by the antibody to which conjugation is done, but which retain the membrane translocation capability which enhances potency) [Hnatowich et al., *J. Nuclear Medicine* 26:503–509 (1985)]. Conjugation of toxins to antibody is done by heterobiofunctional cross-linkers such as N-succinimidyl 3-(2-pyridyldithio) propionate (SPDP) or 2-iminothiolane [Cawley et al., *Cell* 22:563–570 (1980); Goff et al., *Bioconjugate Chemistry* 1:381–386 (1990); and Thorpe et al., *J. Natl. Cancer Inst.,* 79:1011]. In addition, toxins fused to a c-kit binding component of antibody are generated by recombinant expression of genetically-engineered elements of toxin and antibody genes joined as a continuous genetic element.

Prior to diagnostic or therapeutic use, conjugated antibodies are tested to judge their toxic potency, target specificity, in vitro and in vivo stability, and other properties, [Blättler et al., *Cancer Cells* 1:50–55 (1989) and *Immunotoxins,* Edited by A. E. Frankel Kluwer Academic Publishers, Boston (1988)]. It is desired that the toxicity of the toxic agent, and the binding affinity and specificity of the antibody, be minimally affected by the coupling procedures used. Thus conjugates are tested for binding to SCF receptor (see Example 3), and inhibition of SCF binding to SCF receptor (see Example 4). In vitro toxicity toward target cells such as the erythroleukemia cell line OCIM1 is tested by measuring incorporation of labeled compounds into macromolecules in treated versus untreated cell cultures, and more directly by determining the number of cells in treated versus untreated cultures that are able to grow in clonogenic and cell growth back-extrapolation assays. In vivo stability, clearance, and specific toxicity are judged by administration of conjugate to appropriate animal recipients. Such recipients include normal mice and in vivo tumor and leukemia xenograft models comprising human neoplastic cells introduced into immunodeficient strains of mice, such as the nude mouse or SCID mouse.

Example 8

Preparation of Pharmaceutical Composition Containing Monoclonal Antibody SR-1

Pharmaceutical compositions of the present invention include an effective amount of the active ingredient, SR-1, alone or in combination with a suitable buffer, diluent and/or additive. Such compositions are provided as sterile aqueous solutions or as lyophilized or otherwise dried formulations. Typically, antibodies are formulated in such vehicles at concentrations from about 1 mg/ml to 10 mg/ml.

One example of a suitable pharmaceutical composition for injection contains monoclonal antibody SR-1 (1 mg/ml) in a buffered solution (pH 7.0±0.5) of monobasic sodium phosphate (0.45 mg/ml) and Tween 80 (0.2 mg/ml) in sterile H$_2$O.

Example 9

Selection of Cells Containing SCF Receptors a. Selection of Cells Containing SCF Receptors by Direct Immune Adherence with SR-1

Cells expressing SCF receptors were selected by direct immune adherence, and the proliferative potential of these cells was determined in colony assays. Monocyte-depleted normal human marrow mononuclear cells were separated by direct immune adherence with SR-1, and cultured in erythropoietin plus IL-3 in semisolid medium for 14 days. The data represent the average of duplicate plates from 1 of 3 experiments.

The results (Table 4) show a 50-fold enrichment in BFU-E in the SR-1 adherent population of cells. The fraction of BFU-E ranged from 4–7%, and the overall recovery of BFU-E in the SR-1 adherent population was 70%. These results indicate that SR-1 can be used to purify populations of progenitor cells by direct immune adherence.

TABLE 4

ISOLATION OF PROGENITOR CELLS WITH SR-1

| Cells | Colonies/$10^5$ Cells | |
|---|---|---|
|  | BFU-E | CFU-GM |
| Marrow mononuclear | 117 | 151 |
| SR-1 Adherent | 5040 | 840 |
| SR-1 Non-adherent | 6 | 24 |

To determine whether more primitive hematopoietic cells are found in the SR-1 adherent population, the cells were cultured in suspension for 12 days. At 3 day intervals, aliquots of cells were removed and replated in methylcellulose colony assays to quantitate progenitors. The results show that the SR-1 adherent cells generated large numbers of BFU-E and CFU-GM (up to 3-fold above input) throughout the 12 day suspension culture period. The number of BFU-E and CFU-GM in the SR-1 non-adherent population did not increase above input, and continuously declined. This indicates that the SR-1 adherent population of cells contains more primitive hematopoietic cells that are capable of generating progenitor cells.

b. Selection of Cells Containing SCF Receptors by Fluorescence-Activated Cells Sorting with SR-1

Normal human bone marrow mononuclear cells were simultaneously labeled with anti-CD34 (monoclonal antibody 12.8 [Andrews et al., *J. Exp. Med.* 172–355 (1990)] and SR-1, and separated on a FACS as illustrated in Example 10. The fraction of progenitors was determined by colony assays in methylcellulose. The results show that the CD34 positive, SR-1 positive population of cells contained 80% of the BFU-E and 96% of the CFU-GM. The CD34 positive, SR-1 negative population of cells contained 20% of the BFU-E and 4% of the CFU-GM. This indicates that SR-1 identifies a subset of CD34 positive cells that contains the majority of myeloid and erythroid progenitor cells. Furthermore, these progenitor cells can be positively selected by cell sorting with SR-1.

Example 10

Fluorescence Activated Cell Sorting of Cells Displaying SCF Receptors

In fluorescence activated cell sorting (FACS), cells displaying SCF receptors were mixed with the monoclonal antibody SR-1. The SR-1 monoclonal antibody was either (1) conjugated with the fluorescence label FITC or PE; (2) conjugated with biotin and mixed with avidin or streptoavidin which is conjugated with FITC or PE; or (3) further mixed with a goat anti-mouse FITC or a sheep anti-mouse FITC.

Such directly labelled or indirectly labelled SCF-receptor-containing cells were then separated on the basis of the level of fluorescence using standard FACS methods.

What is claimed is:

1. A method of reconstituting hematopoietic cells in a mammal comprising the steps of:
   (a) exposing a mixture of cells containing hematopoietic cells to an antibody or fragment thereof which binds to an epitope on a receptor recognized by human stem cell factor, said epitope being recognized by the monoclonal antibody produced by the hybridoma cell line ATCC No. HB 10716;
   (b) separating cells that bind to the antibody or fragment thereof from cells that do not bind to the antibody or fragment; and
   (c) transplanting the cells that bind to the antibody or fragment thereof, thereby reconstituting hematopoietic cells.

2. The method of claim 1 wherein the cells used for transplantation are hematopoietic cells.

3. The method of claim 1, comprising the steps of:
   exposing the cells obtained in step (b) to at least a second antibody or fragment thereof which specifically binds a cell surface protein that occurs on subpopulations of the cells;
   separating the subpopulations of cells that bind to the second antibody or fragment thereof from cells that do not bind to the second antibody or fragment thereof; and
   transplanting the subpopulations of cells that bind to the second antibody or fragment thereof.

4. The method of claim 1 wherein the antibody is produced from hybridoma cell line ATCC No. HB 10716.

5. The method of claim 1 wherein the mixture of cells of step (a) comprise bone marrow cells, blood cells or tissue cells.

6. The method of claim 1 wherein step
   (b) comprises column chromatography, fluorescence-activated cell sorting, magnetic bead separation, or direct immune adherence.

7. The method of claim 3 wherein the second antibody is an anti-CD34 antibody.

8. A method of reconstituting hematopoietic cells in a mammal comprising the steps of:
   (a) exposing a mixture of cells containing hematopoietic cells to an antibody or fragment thereof wherein the antibody or fragment specifically binds a receptor recognized by human stem cell factor;
   (b) separating cells that bind to the antibody or fragment thereof from cells that do not bind to the antibody or fragment; and
   (c) transplanting the cells that bind to the antibody or fragment thereof, thereby reconsituting hematopoietic cells,
   wherein the antibody or fragment thereof binds the receptor in a manner that inhibits binding of human stem cell factor to the receptor by at least 50%.

9. The method of claim 8 comprising the steps of:
   exposing the cells obtained in step (b) to at least a second antibody or fragment thereof which specifically binds a cell surface protein that occurs on subpopulations of the cells;
   separating the subpopulations of cells that bind to the second antibody or fragment thereof from cells that do not bind to the second antibody or fragment thereof; and
   transplanting the subpopulations of cells that bind to the second antibody or fragment thereof.

10. The method of claim 8 wherein the antibody or fragment thereof inhibits binding by at least 75%.

11. The method of claim 8 wherein the antibody or fragment thereof inhibits binding by at least 90%.

12. A method of reconstituting hematopoietic cells in a mammal comprising the steps of:
   (a) exposing a mixture of cells containing hematopoietic cells to an antibody or fragment thereof wherein the antibody or fragment specifically binds a receptor recognized by human stem cell factor;
   (b) separating cells that bind to the antibody or fragment thereof from cells that do not bind to the antibody fragment; and
   (c) transplanting the cells that bind to the antibody or fragment thereof, thereby reconstituting hematopoietic cells,
   wherein the antibody or fragment binds the receptor in a manner that decreases the growth rate of receptor-containing cells in the presence of human stem cell factor by at least one half.

13. The method of claim 12 comprising the steps of:
   exposing the cells obtained in step (b) to at least a second antibody or fragment thereof which specifically binds a cell surface protein that occurs on subpopulations of the cells;
   separating the subpopulations of cells that bind to the second antibody or fragment thereof from cells that do not bind to the second antibody or fragment thereof; and
   transplanting the subpopulations of cells that bind to the second antibody or fragment thereof.

14. The method of claim 12 wherein the antibody or fragment thereof decreases the growth rate by at least one tenth.

15. The method of claim 12 wherein the antibody or fragment thereof decreases the growth rate by at least one hundredth.

16. The method of claims 8 or 12 wherein the mixture of cells in step (a) comprise bone marrow cells, blood cells or tissue cells.

17. The method of claims 8 or 12 wherein step (b) comprises column chromatography, fluorescence-activated cell sorting, magnetic bead separation or direct immune adherence.

18. The method of claims 9 or 13 wherein the second antibody is an anti-CD34 antibody.

* * * * *

UNITED STATES PATENT AND TRADEMARK OFFICE
CERTIFICATE OF CORRECTION

PATENT NO. : 5,906,938
DATED : May 25, 1999
INVENTOR(S) : Virginia C. Broudy and Nancy Lin It is certified that error appears in the above-identified patent and that said Letters Patent is hereby corrected as shown below:

Column 3, line 51, change "106601074" to --1066-1074--.

Column 8, line 41, change "in ingredient" to --ingredient --.

Column 9, line 30, delete -- co-pending U.S. Patent Applications 07/589,701, 07/573,616, and 07/537,198, filed October 1, 1990, August 24, 1990, and June 11, 1990, respectively --.

Signed and Sealed this

Fourteenth Day of December, 1999

Attest:

Q. TODD DICKINSON

Attesting Officer

Acting Commissioner of Patents and Trademarks